United States Patent [19]

Martinez

[11] Patent Number: 4,753,234

[45] Date of Patent: Jun. 28, 1988

[54] SURGICAL CUTTING INSTRUMENT HAVING A OFFSET PROBE FOR OPHTHALMIC SURGERY

[76] Inventor: Miguel Martinez, 1084 Desert Hills Dr., Green Valley, Ariz. 85614

[21] Appl. No.: 925,978

[22] Filed: Nov. 3, 1986

[51] Int. Cl.⁴ .............................................. A61F 17/32
[52] U.S. Cl. ...................................... 128/305; 604/22; 30/241
[58] Field of Search ................................ 433/121–123; 604/22; 128/305, 752–755; 30/241, 182

[56] References Cited

U.S. PATENT DOCUMENTS

| | | | |
|---|---|---|---|
| 3,412,466 | 11/1968 | Kurosaki | 30/241 |
| 3,561,429 | 2/1971 | Jewett et al. | 128/305 |
| 4,368,734 | 1/1983 | Banko | 128/305 |
| 4,517,977 | 5/1985 | Frost | 604/22 |
| 4,577,629 | 3/1986 | Martinez | 604/22 |

Primary Examiner—C. Fred Rosenbaum
Assistant Examiner—J. L. Kruter
Attorney, Agent, or Firm—Epstein & Edell

[57] ABSTRACT

A surgical cutting instrument, particularly useful for ophthalmic surgery, includes a cylindrical body, a piston disposed for reciprocating movement in a chamber in the body and a probe having an elongate tubular outer probe member with a closed distal end and a port adjacent thereto and an elongate inner probe member slidably disposed in the outer probe member with a distal end movable across the port to provide a cutting action and a portion mounted to the piston such that the probe is positioned parallel to the longitudinal axis of the cylindrical body and axially offset therefrom such that the inner and outer probe members are in positive alignment and not subject to relative rotation and inadvertent misalignment. An evacuation tube receives cut material from the probe passing through the surgical cutting instrument and a supply tube supplies pressure to the chamber to reciprocate the piston.

15 Claims, 2 Drawing Sheets

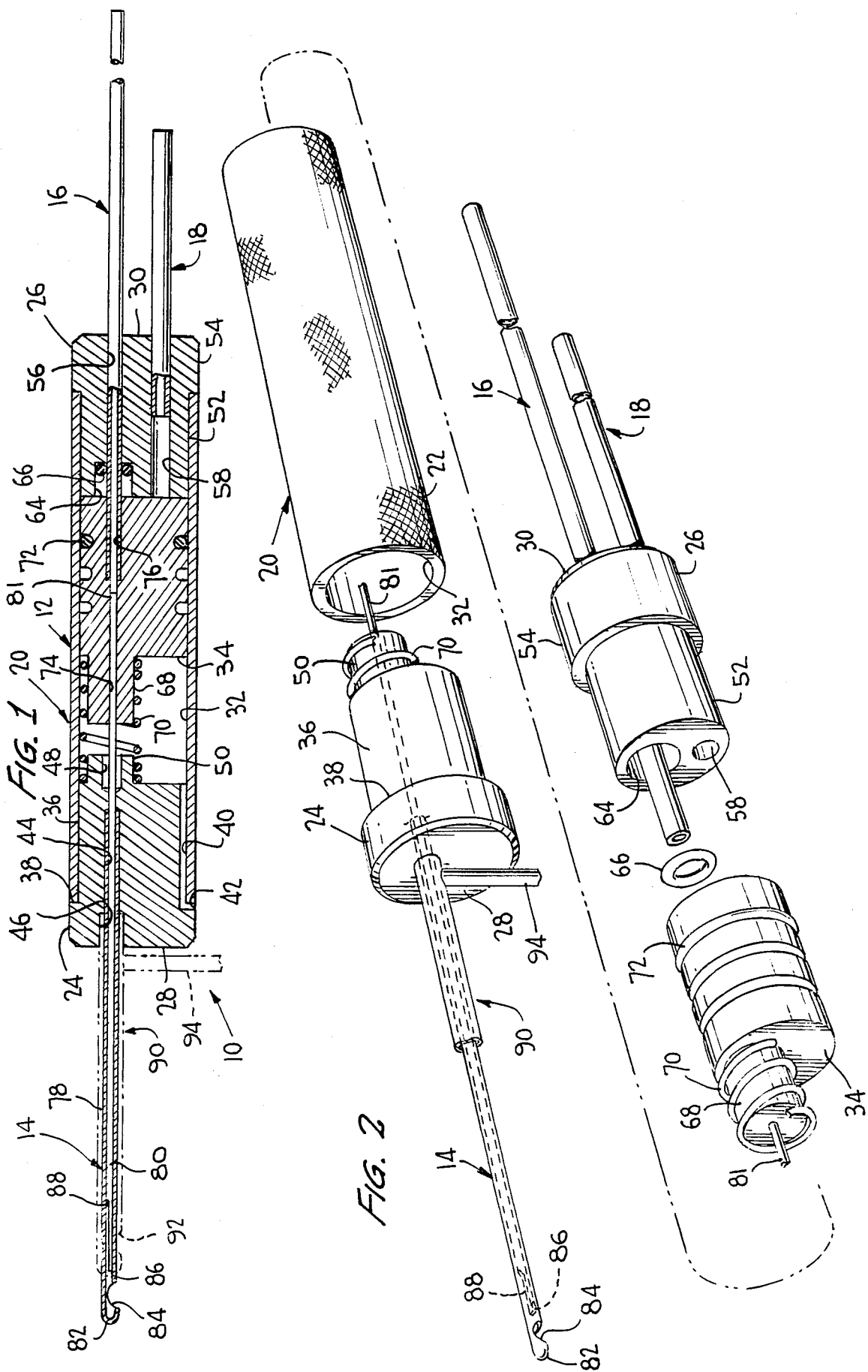

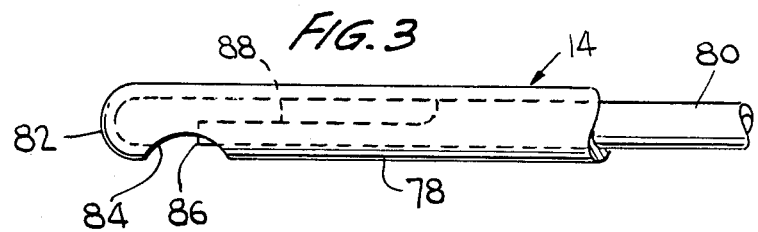
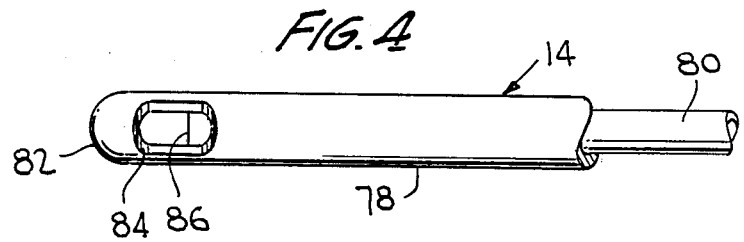
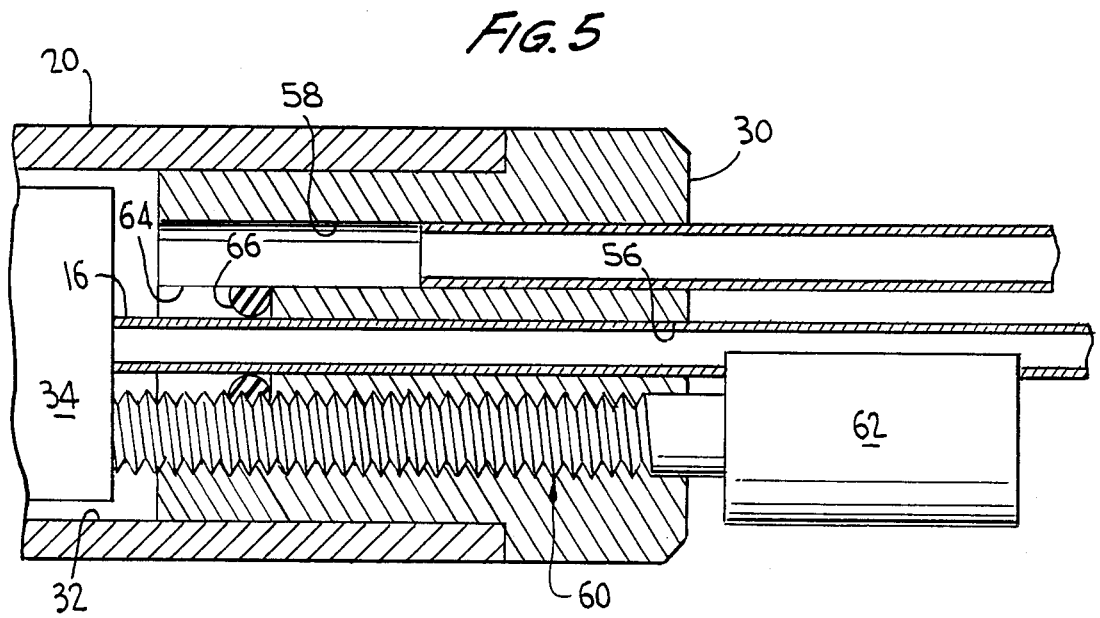
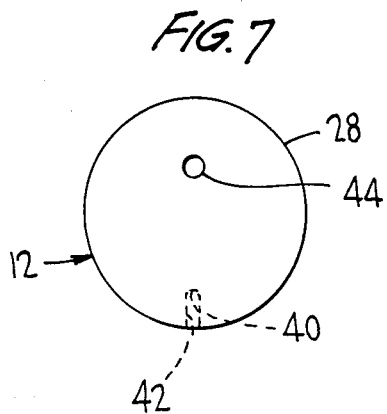
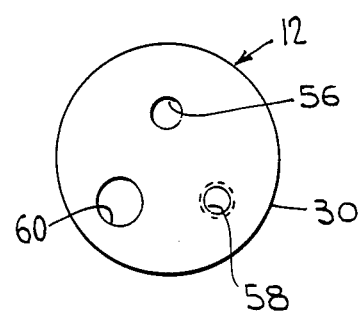

SURGICAL CUTTING INSTRUMENT HAVING A OFFSET PROBE FOR OPHTHALMIC SURGERY

BACKGROUND OF THE INVENTION

1. Technical Field

The present invention pertains to surgical cutting instruments for use in ophthalmic surgery and, more particularly, to such surgical cutting instruments designed to be economically disposable.

2. Discussion of the Prior Art

Many ophthalmic surgeons presently use surgical cutting instruments for cutting and removing vitreous, blood clots, cataracts, lenses and other matter from the eye. Such surgical cutting instruments use various means to cut or separate the matter from the eye including pulsating fluid jets or mechanical cutting or shearing mechanisms, such as rotating members or reciprocating members, the latter being exemplified by U.S. Pat. No. 3,776,238 to Peyman et al, U.S. Pat. No. 3,884,238 to O'Malley et al, U.S. Pat. No. 3,994,297 to Kopf, U.S. Pat. No. 4,011,869 to Seiler, Jr., U.S. Pat. No. 4,246,902 to Martinez and U.S. Pat. No. 4,314,560 to Helfgott et al. While such surgical cutting instruments have been well received and are commonly used in ophthalmic surgery, there is a need for an economically disposable surgical cutting instrument that can be available along with other instruments and materials required for surgery, particularly cataract surgery, in a sterilized package or kit. However, any economically disposable surgical cutting instrument must still provide precise cutting and adequate suction and evacuation of cut material and must be designed and shaped to facilitate manipulation by a surgeon. The above mentioned patents disclose surgical cutting instruments with a tubular outer member having a tubular inner member sliding therein and reciprocated by various means of motive power. These instruments have the disadvantages of not being economically disposable in that they include a number of intricate parts, require precision machining and tooling, requiring complicated assembly procedures, and requiring disassembly for sharpening and sterilization.

The surgical cutting instrument of U.S. Pat. No. 4,577,629 to Martinez has been well accepted as an economically disposable surgical cutting instrument for use in ophthalmic surgery while providing precision cutting and sufficient evacuation of cut material; however, alignment of the distal ends of the inner and outer probe members, which is crucial to proper precision cutting action, requires rotation of the piston via a tool engaging a slot in the piston prior to screwing the rear plug into the body. This alignment step increases the cost of assembly and continued alignment is dependent upon frictional engagement of the piston and seals with the body thereby requiring careful handling and close inspection during use to assure that alignment is maintained and misalignment does not occur inadvertently.

SUMMARY OF THE INVENTION

Accordingly, it is a primary object of the present invention to provide an economically disposable surgical cutting instrument for use in ophthalmic surgery overcoming the above mentioned disadvantages of the prior art while providing precision cutting, sufficient evacuation of cut material and positive alignment of the distal ends of the inner and outer probe members.

Another object of the present invention is to construct a surgical cutting instrument of a minimal number of uncomplicated parts that can be inexpensively produced and assembled.

A further object of the present invention is to assemble a surgical cutting instrument with positive alignment of a distal cutting end of an inner probe member with a cutting port adjacent a distal end of an outer probe member without requiring additional structural interconnection between a piston mounting the inner probe member and a cylindrical body such that inadvertent misalignment cannot occur.

The present invention has another object in that an elongate probe of a surgical cutting instrument is offset from the longitudinal axis of a cylindrical body of the instrument to provide positive alignment of a port in the outer probe member with an inner cutting probe member and to position the probe in close proximity to the periphery of the body of the instrument to reduce the space between the instrument and the orbital rim and, thus, facilitate insection of the probe in the anterior chamber.

Some of the advantages of the present invention over the prior art are that assembly is facilitated by force fitting, cost of parts and assembly is minimized and the surgical cutting instrument is small and light weight to be easily handled by a surgeon with no probe alignment.

The present invention is generally characterized in a surgical cutting instrument useful in ophthalmic surgery including a cylindrical, hollow body having a front end, a rear end and a chamber disposed between the front and rear ends; a piston disposed in the chamber to be moveable in a reciprocating manner toward and away from the front end; a probe extending from the front end of the body at a position parallel to and offset from the longitudinal axis of the body including an elongate tubular outer probe member mounted to the front end of the body and having a closed distal end and a port adjacent the distal end and an elongate inner probe member slidably disposed in the outer probe member and having a distal end movable across the port to provide a cutting action, a portion mounted to the piston and passage means extending along the inner probe member from the distal end to the portion mounted to the piston; evacuating means communicating with the probe to permit passage of cut material through the surgical cutting instrument; and supply means communicating with the chamber to supply pressure to move the piston to reciprocate the inner probe member in the outer probe member to produce the cutting action.

Other objects and advantages of the present invention will become apparent from the following description of the preferred embodiment taken in conjunction with the accompanying drawings.

BRIEF DESCRIPTION OF THE DRAWINGS

FIG. 1 is a longitudinal cross section of a surgical cutting instrument according to the present invention.

FIG. 2 is an exploded isometric view of the surgical cutting instrument of FIG. 1.

FIGS. 3 and 4 are broken side and top views, respectively, of the cutting tip of the surgical cutting instrument of FIG. 1.

FIG. 5 is a partial longitudinal cross section of the surgical cutting instrument of FIG. 1 showing the adjustment screen.

FIG. 6 is a rear end view of the surgical cutting instrument of FIG. 1.

FIG. 7 is a front end view of the surgical cutting instrument of FIG. 1.

DESCRIPTION OF THE PREFERRED EMBODIMENT

A surgical cutting instrument 10 according to the present invention is shown in FIGS. 1 and 2 and includes a cylindrical hollow body 12 with a probe 14 extending from a front end thereof at a position parallel to and offset from the longitudinal axis of the body and an evacuating tube 16 and a pressure supply tube 18 extending from a rear end of the body. The surgical cutting instrument 10 can be utilized with any suitable source of suction communicating with evacuating tube 16 and any suitable pulsed source of pressurized fluid, preferably air, communicating with supply tube 18. Preferably, the source of pressurized fluid is capable of supplying pressure pulses at an adjustable frequency of up to 400 pulses per minute and of supplying a single pulse upon actuation of a switch to produce a single pulse and a corresponding single cutting stroke. The suction applied to evacuating tube 16 is controlled in conventional manner by a foot or hand operated device coupled with the source of suction.

The body 12 is formed of a cylindrical barrel 20, preferably made of aluminum, having a knurled outer surface 22, the body having an outer diameter and a length from a front end 24 to a rear end 26 to be easily held and manipulated by a surgeon. A front plug 28 is force-fit or threaded into the open front end of barrel 20 and a rear plug 30 is force-fit or screwed into the open rear end of barrel 20 to define therebetween a chamber 32 in which is disposed a piston 34 to be movable in a reciprocating manner toward and away from the front end 24. The front and rear plugs are preferably made of plastic for reduced weight and ease of manufacture and assembly.

The front plug 28 has a stem 36 received in the open front end of barrel 20 with a force-fit and a head 38 abutting the end of the barrel, the stem 36 and the head 38 having aligned grooves 40 and 42 formed therein, respectively, to provide a passage communicating with chamber 32 and externally in a direction transverse to or radially outward of the longitudinal axis of the surgical cutting instrument 10. A bore 44 extends longitudinally through front plug 28 parallel to and offset from the axis of the front plug, as shown in FIG. 7, and the bore has a counter bore of enlarged diameter 46 adjacent its external end and a conical or tapered increased diameter portion 48 at its internal end in a cylindrical protrusion 50 having an axis aligned with probe 14.

The rear plug 30 has a stem 52 received in the open rear end of barrel 20 with a force-fit and a head 54 abutting the end of the barrel. As best shown in FIGS. 5 and 6, bores 56, 58 and 60 are equally angularly spaced around the axis of the rear plug and extend through the plug parallel to but offset from the axis, the bore 56 receiving the evacuating tube 16, the bore 58 receiving the supply tube 18 and the bore 58 being threaded to receive an adjustment screw 60 having a head 62 external of the rear plug. The bore 56 has a counterbore 64 at its internal end, and an o-ring seal 66 is disposed in counterbore 64 in sealing engagement with the rear plug 30 and the evacuating tube 16.

The piston 34 is generally cylindrical in configuration and is preferably made of plastic, the piston having a length less than the length of chamber 32 by an amount equal to the maximum stroke desired for the cutting probe. A cylindrical protrusion 68 extends from the front end of the piston of a diameter corresponding to the diameter of cylindrical protrusion 50 of the front plug 28, and a helical spring 70 is mounted in compression between the front end of the piston and the internal end of the front plug around cylindrical protrusions 50 and 68 in order to bias the piston toward the rear plug 30. The piston 34 carries an o-ring seal 72 mounted in an annular groove to engage the internal wall of chamber 32 with two additional annual grooves being provided for molding purposes to minimize shrinkage of plastic. A bore 74 extends longitudinally through piston 34 and a counterbore 76 of enlarged diameter at its rear end to receive evacuating tube 16, the bore being aligned with bore 44 in front plug 28 to be parallel to and offset from the axis of the longitudinal cylindrical body 12.

The probe 14 is formed of an elongate tubular outer probe member 78, preferably made of 20 gauge stainless steel, and an elongate tubular inner probe member 80 preferably made of 23 gauge stainless steel. The outer probe member 78 has a proximal end secured in bore 44 in front plug 28 with a force-fit while the inner member 76 is mounted to piston 34 via a proximal end 81 force-fit in bore 74. Inner probe member 80 has a diameter to permit reciprocating sliding movement in outer probe member 78. As best shown in FIGS. 3 and 4, the distal end 82 of outer probe member 78 is closed and has a rounded configuration, and a port 84 is cut in the sidewall of the outer probe member adjacent distal end 82. The distal end 86 of inner probe member 80 is cut-away at 88 to have a reduced cross section defining a cutting blade to provide shearing cutting action as it is moved across port 84 toward the closed end of the outer probe member.

As will be appreciated from the above, the surgical cutting instrument 10 is constructed of a minimal number of components and can be simply assembled by force fitting the outer probe member 78 in front plug 28, force fitting front plug 28 in the front end of barrel 20, force fitting inner probe member 80 in axially offset bore 74 in piston 34 in a position to be rotationally aligned with port 84 in the outer probe member, placing spring 70 around cylindrical protrusion 50, inserting the inner probe member in the outer probe member via tapered portion 48 and the piston carrying the o-ring seal in chamber 32 from the rear end of the barrel, force fitting evacuating tube 16 and supply tube 18 in rear plug 30, threading adjustment screw 62 in rear plug 30 and force fitting the rear plug in the rear end of the barrel with the inner end of evacuating tube 16 received in counterbore 76 of the axially offset bore 74 in piston 34.

In use, the surgical cutting instrument 10 will be coupled with a suitable controlled suction source via a length of flexible tubing connected with evacuating tube 16, which is preferably rigid and made of stainless steel, and with a suitable controlled pulsed pneumatic source via a length of flexible tubing connected with supply tube 18, which is preferably rigid and made of stainless steel. The surgeon, in utilizing the surgical cutting instrument to remove material from the eye, adjusts the frequency of the pressure pulses as desired to control the frequency and number of cutting strokes of the probe. With no pressure applied to supply tube 18, spring 70 biases piston 34 against rear plug 30 which moves the inner probe member away from the closed end of the outer probe member to move the distal end 86 thereof away from port 84. When a pressure pulse is supplied to supply tube 18, the force of spring 70 is overcome, and piston 34 is moved toward the front of body 12 until it contacts the end of cylindrical protrusion 50, air in the chamber being vented through the passage formed by grooves 40 and 42 and expelled radially away from the surgical site. Movement of the piston 34 causes movement of the distal end 86 of inner probe member 80 across port 84 to cut or shear material extending into the port. Suction applied to the tip of the probe 14 via evacuating tube 16 and the passage formed along inner probe member 80 withdraws the cut material from the surgical cutting instrument and also enhances cutting operation by drawing material to be cut into port 84 prior to the cutting stroke of the inner probe member 80. At the end of the pressure pulse, the removal of pressure from the rear end of the piston allows the spring 70 to force the piston back against the rear plug with air supplied to chamber 32 at the front end of the piston via the passage formed by grooves 40 and 42. Adjustment of the supply source permits the frequency and number of pressure pulses and, therefore, cutting strokes to be controlled, and the application of suction can be controlled by the surgeon via a manually-operated device.

By offsetting the probe 14 and the piston bore 74 from the axis of the body 12, the longitudinal insertion of inner probe member 80 in outer probe member 78 prevents piston 34 from rotating in chamber 34 thus positively aligning the cutting distal end 86 of the inner probe member with the port 84 in the outer probe member. That is, once the outer probe member is secured in front plug 28 and the inner probe member is mounted to piston 34 and rotationally positioned to align distal end 86 with port 84, the alignment of the probe members is assured, and inadvertent misalignment is prevented since the inner probe member cannot rotate in the outer probe member. Additionally, the axial offset of the probe places the cutting tip closer to the peripheral edge of the body to reduce the space between the instrument and the orbital rim and to facilitate insertion, manipulation and observation by the surgeon.

The adjustment screw 60 can be rotated via head 62 to move the screw into the chamber 32 and limit the opening or noncutting stroke of the inner member. As shown in FIG. 5, adjustment screw 60 has been turned to move the end into chamber 32 beyond the internal end of rear plug 30 such that the end of adjustment screw 60 acts as a stop abutting the rear end of piston 34 to limit rearward movement of the piston and therefore inner probe member 80. The adjustment screw thus permits the opening at port 84 to be adjusted to control suction and cutting stroke to permit precision control by the surgeon over the cutting operation.

Counterbore 46 is positioned to receive the proximal end of a stainless steel irrigating sleeve 90, as shown in dashed lines in FIG. 1, extending coaxially around probe 14 and having a port 92 adjacent the distal end thereof to supply irrigating fluid to the surgical cutting site. The irrigating fluid can be supplied from any suitable source via a coupling 94 communicating with a sleeve 90.

Inasmuch as the present invention is subject to many variations, modifications and changes in detail, it is intended that all subject matter discussed above or shown in the accompanying drawings be interpreted as illustrative and not in a limiting sense.

What is claimed is:

1. A surgical instrument useful in ophthalmic surgery comprising:
   a cylindrical, hollow body having a longitudinal axis, a front end, a rear end and a chamber disposed between said front and rear ends;
   a piston means disposed in said chamber to be movable in a reciprocating manner toward and away from said front end and having a longitudinal axis;
   probe means extending form said front end of said body at a position parallel to and offset from said longitudinal axis of said body including an elongate, tubular outer probe member having a closed distal end and a port adjacent said distal end, and an elongate inner probe member slidably disposed in said outer probe member and having a distal end movable across said port to provide a cutting action, a portion mounted to said piston means to prevent rotation of said piston means and said inner probe member a position offset from said longitudinal axis of said piston and passage means extending along said inner probe member from said distal end to said portion mounted to said piston means;
   evacuating means communicating with said probe means to permit passage of cut material through said surgical cutting instrument; and
   supply means communicating with said chamber to supply pressure to move said piston means to reciprocate said inner probe member in said outer probe member to produce said cutting action.

2. A surgical cutting instrument as recited in claim 1 wherein said inner probe member is tubular along a substantial portion of its length to define said passage means and is cutaway at said distal end to have a reduced cross section defining a cutting blade aligned with said port in said distal end of said outer probe member to provide a shearing cutting action.

3. A surgical instrument as recited in claim 2 wherein said piston means has a longitudinal bore therethrough off said longitudinal axis of said piston means and said longitudinal axis of said body, and said inner probe member has a proximal end received in said piston means bore.

4. A surgical instrument as recited in claim 3 wherein said piston means has a rear end, said piston means bore includes a counterbore at said rear end of said piston means, and said evacuating means includes a rigid tube received in said piston means counterbore.

5. A surgical instrument as recited in claim 3 wherein said body includes a cylindrical barrel having an open front end and an open rear end, a front plug received in said open front end of said barrel having a longitudinal bore therethrough offset from the said longitudinal axis of said body and receiving said probe means with said outer probe member secured in said front plug bore, and a rear plug received in said open rear end of said barrel having a first longitudinal bore therethrough aligned with said piston means bore and a second longitudinal bore therethrough, said evacuating means includes a rigid evacuating tube received in said first bore, and said supply means includes a rigid supply tube received in said second bore in said rear plug.

6. A surgical instrument as recited in claim 4 wherein said body includes a cylindrical barrel having an open front end and on open rear end, a front plug received in said open front end of said barrel having a longitudinal bore therethrough offset from said longitudinal axis of said body and receiving said probe means with said outer probe member secured in said front plug bore, and a rear plug received in said open rear end of said barrel having a first longitudinal bore therethrough aligned with said piston means bore and receiving said rigid evacuating tube and a second longitudinal bore therethrough and said supply means includes a rigid supply tube received in said second bore in said rear plug.

7. A surgical cutting instrument as recited in claim 6 wherein said rear plug has a threaded longitudinal bore therethrough threadedly receiving an adjustment screw having an end movable into said chamber to abut said piston means and limit movement of said inner probe member.

8. A surgical cutting instrument as recited in claim 7 wherein said front plug has a cylindrical protrusion extending into said chamber, and said piston means has a cylindrical protrusion facing and aligned with said front plug cylindrical protrusion, and further comprising a helical spring mounted in compression between said front plug and said piston means and around said cylindrical protrusions to bias said piston means away from said front plug.

9. A surgical cutting instrument as recited in claim 8 wherein said front plug has a front end and said front plug bore has a counterbore at said front end, and further comprising an irrigating sleeve extending coaxially around said probe means and having a proximal end received in said front plug counterbore, a distal end having an irrigating port therein disposed adjacent said distal end of said outer probe member and a coupling for supplying irrigating fluid to said irrigating sleeve for exit at said irrigating port.

10. A surgical instrument as recited in claim 1 wherein said piston means has a rear end, and a bore in said rear end of said piston means, and said evacuating means includes a rigid tube received in said piston means counterbore.

11. A surgical cutting instrument as recited in claim 1 wherein said body includes a rear plug having a threaded longitudinal bore therethrough threadedly receiving an adjustment screw having an end movable into said chamber to abut said piston means and limit movement of said inner probe member.

12. A surgical cutting instrument as recited in claim 1 wherein said body includes a front plug having a longitudinal bore therethrough offset from said longitudinal axis of said body and receiving said probe means, said front plug and said longitudinal bore including a counterbore at said front end, and further comprising an irrigating sleeve extending coaxially around said probe means and having a proximal end received in said front plug counterbore, a distal end having an irrigating port therein disposed adjacent said distal end of said outer probe member and a coupling for supply irrigating fluid to said irrigating sleeve for exit at said irrigating port.

13. A surgical instrument as recited in claim 1 wherein said piston means has a longitudinal bore therethrough offset from said longitudinal axis of said piston means and said longitudinal axis of said body, and said inner probe member has a proximal end received in said piston means bore.

14. A surgical cutting instrument useful in ophthalmic surgery comprising:
a body having a front end, a rear end and a chamber disposed between said front and rear ends;
a piston means disposed in said chamber to be movable in a reciprocating manner toward and away from said front end, said piston means having a longitudinal axis;
probe means extending from said front end of said body at a position parallel to and offset from said longitudinal axis of said piston means including an elongate, tubular outer probe member having a closed distal end and a port adjacent said distal end, and an elongate inner probe member slidably disposed in said outer probe member and having a distal end movable across said port to provide a cutting action, a portion mounted to said piston means at a position offset from said longitudinal axis of said piston means to prevent rotation of said piston means and said inner probe member and passage means extending along said inner probe member from said distal end to said portion mounted to said piston;
evacuating means communicating with said probe means to permit passage of cut material through said surgical cutting instrument; and
supply means communicating with said chamber to supply pressure to move said piston means to reciprocate said inner probe member in said outer probe member to produce said cutting action.

15. A surgical instrument as recited in claim 14 wherein said piston means has a longitudinal bore therethrough offset from said longitudinal axis of said piston means and said inner probe member has a proximal end received in said piston means bore.

* * * * *